United States Patent
Sakata et al.

(10) Patent No.: US 9,505,850 B2
(45) Date of Patent: Nov. 29, 2016

(54) ENDOTOXIN ADSORBENT

(71) Applicants: NATIONAL UNIVERSITY CORPORATION KUMAMOTO UNIVERSITY, Kumamoto (JP); JNC CORPORATION, Tokyo (JP)

(72) Inventors: Masayo Sakata, Kumamoto (JP); Masami Todokoro, Tokyo (JP)

(73) Assignees: NATIONAL UNIVERSITY CORPORATION KUMAMOTO UNIVERSITY, Kumamoto (JP); JNC CORPORATION, Tokyo (JP)

( * ) Notice: Subject to any disclaimer, the term of this patent is extended or adjusted under 35 U.S.C. 154(b) by 0 days.

(21) Appl. No.: 14/404,479

(22) PCT Filed: May 29, 2013

(86) PCT No.: PCT/JP2013/064905
§ 371 (c)(1),
(2) Date: Nov. 28, 2014

(87) PCT Pub. No.: WO2013/180176
PCT Pub. Date: Dec. 5, 2013

(65) Prior Publication Data
US 2015/0112050 A1   Apr. 23, 2015

(30) Foreign Application Priority Data

May 30, 2012   (JP) .................. 2012-123281

(51) Int. Cl.
| | |
|---|---|
| *C08B 37/16* | (2006.01) |
| *B01J 20/30* | (2006.01) |
| *C08L 5/16* | (2006.01) |
| *C08G 18/64* | (2006.01) |
| *B01J 20/26* | (2006.01) |
| *C07H 1/06* | (2006.01) |
| *C07H 21/02* | (2006.01) |
| *C07H 21/04* | (2006.01) |
| *B01J 20/286* | (2006.01) |
| *B01J 20/32* | (2006.01) |

(52) U.S. Cl.
CPC .......... *C08B 37/0012* (2013.01); *B01J 20/267* (2013.01); *B01J 20/286* (2013.01); *B01J 20/30* (2013.01); *B01J 20/3042* (2013.01); *B01J 20/321* (2013.01); *B01J 20/3204* (2013.01); *B01J 20/3212* (2013.01); *B01J 20/3274* (2013.01); *B01J 20/3282* (2013.01); *C07H 1/06* (2013.01); *C07H 21/02* (2013.01); *C07H 21/04* (2013.01); *C08B 37/0015* (2013.01); *C08G 18/6484* (2013.01); *C08L 5/16* (2013.01)

(58) Field of Classification Search
None
See application file for complete search history.

(56) References Cited

U.S. PATENT DOCUMENTS

| | | | |
|---|---|---|---|
| 4,576,928 | A | 3/1986 | Tani et al. |
| 5,747,663 | A | 5/1998 | Colpan et al. |
| 2002/0130082 | A1 | 9/2002 | Todokoro et al. |
| 2007/0213258 | A1 | 9/2007 | Nakayama et al. |
| 2008/0312575 | A1 | 12/2008 | Graziani et al. |

FOREIGN PATENT DOCUMENTS

| | | |
|---|---|---|
| JP | 58-171404 | 10/1983 |
| JP | 59-193135 | 11/1984 |
| JP | 60-20924 | 2/1985 |
| JP | 60-11961 | 3/1985 |
| JP | 03-296516 | 12/1991 |
| JP | 04-256438 | 9/1992 |
| JP | 07-322823 | 12/1995 |
| JP | 09-508406 | 8/1997 |
| JP | 10-195108 | 7/1998 |
| JP | 10-225515 | 8/1998 |
| JP | 2000-189792 | 7/2000 |
| JP | 2001-504879 | 4/2001 |
| JP | 2002-263486 | 9/2002 |
| JP | 2003-226737 | 8/2003 |
| JP | 2003-226755 | 8/2003 |
| JP | 2006-083379 | 3/2006 |
| JP | 2006-143953 | 6/2006 |
| JP | 3817808 | 9/2006 |
| JP | 2007-145743 | 6/2007 |
| JP | 2009-502905 | 1/2009 |
| JP | 4683632 | 5/2011 |
| WO | 9822197 | 5/1998 |

OTHER PUBLICATIONS

Andrew C. Issekutz, "Removal of Gram-Negative Endotoxin from Solutions by Affinity Chromatography", Journal of Immunological Methods, Feb. 1983, p. 275-281, vol. 61.

Montbriand et al., "Improved method for the removal of endotoxin from DNA", Journal of Biotechnology, Jan. 1996, p. 43-46, vol. 44.

Hirayama et al., "Chromatographic removal of endotoxin from protein solutions by polymer particles", Journal of Chromatography B, Dec. 2002, p. 419-432, vol. 781.

Petsch et al., "Endotoxin removal from protein solutions", Journal of Biotechnology, Jan. 2000, p. 97-119, vol. 76.

(Continued)

*Primary Examiner* — Layla Berry
(74) *Attorney, Agent, or Firm* — Jianq Chyun IP Office

(57) ABSTRACT

A means for selectively removing ET under coexistence of a substance showing a negative charge, such as nucleic acid is described. Endotoxin is selectively removed by bringing a polymer obtained by crosslinking cyclodextrin with an isocyanate-based crosslinking agent in contact with a solution containing endotoxin and the substance showing the negative charge such as nucleic acid.

10 Claims, 3 Drawing Sheets

(56) References Cited

OTHER PUBLICATIONS

"International Preliminary Report on Patentability; this report contains the following items :Form PCT/IB/373, PCT/ISA237(cover sheet), PCT/ISA237(Box No. 1),PCT/ISA237(Box No. V)," mailed on Dec. 2, 2014, which is English translation of "Written Opinion of the International Searching Authority", p. 1-p. 13.

"International Search Report (Form PCT/ISA/210)", mailed on Aug. 6, 2013, with English translation thereof, p. 1-p. 4.

Sakata et al., "Selective Removal of Endotoxin from a DNA Solution by Cross-linked Cyclodextrin Beads", Analytical Sciences Feb. 2011, p. 213-216, vol. 27, The Japan Society for Analytical Chemistry, Japan.

ENDOTOXIN ADSORBENT

CROSS-REFERENCE TO RELATED APPLICATION

This application is a 371 application of an international PCT application serial no. PCT/JP2013/064905, filed on May 29, 2013, which claims the priority benefit of Japan application no. 2012-123281, filed on May 30, 2012. The entirety of each of the above-mentioned patent applications is hereby incorporated by reference herein and made a part of this specification.

TECHNICAL FIELD

The present invention relates to an endotoxin adsorbent, and a method for removing endotoxin (hereinafter, also referred to as "ET") using the same. In particular, the invention relates to a method for selectively removing ET under coexistence of an acidic substance such as DNA.

BACKGROUND ART

ET is a toxic substance mainly formed of lipopolysaccharide existing in a cell wall outer membrane of gram-negative bacteria, and freed therefrom when the bacteria are killed. When ET is incorporated into a living body by contaminating of ET to an injectable pharmaceutical preparation or the like, ET causes adverse action such as fever and ET shock thereon. Moreover, ET can act also on a cell itself, and therefore has possibility of influencing an experiment using various kinds of cells. In order to prevent the adverse action of ET, research has been conducted on a method for removing ET from an injectable solution, a substance in contact with a bodily fluid, a laboratory reagent or the like.

As the method for removing ET, an adsorption process by activated carbon or an ion exchanger, a filtration process using a membrane, a membrane filter or the like, a decomposition process by high temperature and high pressure treatment, acid treatment or alkaline treatment have been known so far. In particular, as a method for adsorbing ET to remove the same, an adsorbent using as a ligand polymyxin being a basic antibiotic (see Non-patent literature No. 1, Patent literature No. 1, Patent literature No. 2, for example), and an adsorbent using as a ligand amikacin being a basic antibiotic or the like in a similar manner (see Patent literature No. 3, for example) or the like has been known. The adsorbents using the antibiotics as the ligands are known to adsorb ET, but simultaneously nucleic acid such as DNA also, and are unsuitable for purification of the nucleic acid. For example, in an experiment of removing ET, using polymyxin-agarose, from a DNA solution, a recovery ratio of DNA is 60 at a maximum, and more specifically, at least 40%; of DNA is removed together with ET (see Non-patent literature No. 2, for example).

Research has also been conducted on a cationic (basic) adsorbent produced by introducing an amino group thereinto. For example, a cationic adsorbent produced by allowing diamine to react with methyl polyglutamate, and introducing an amino group thereinto is known (see Patent literature No. 4, for example). The adsorbent has a feature in which the adsorbent has a pore size of 1,000 or less in terms of molecular weight of dextran and is substantially non-porous, and thus can selectively remove ET under coexistence of albumin.

Research has also been conducted on an adsorbent using as a ligand a polymer cationic substance. As the polymer, polyethyleneimine, polyallylamine, polylysine or the like is used (see Non-patent literature No. 3 and Non-patent literature No. 4, for example). Among the absorbents, an adsorbent using epsilon polylysine as the ligand can remove ET from a protein solution particularly when exclusion limit molecular weight of a base material is 6,000 or less (see Patent literature No. 5, for example). The adsorbents using the basic (cationic) substances as the ligands can selectively remove ET from the protein solution, as in the case of the adsorbent in which epsilon polylysine is immobilized, but can selectively remove no ET from a solution of nucleic acid such as DNA. Meanwhile, report has been made on an adsorbent using as a ligand epsilon polylysine in which an amino group is partially modified with glycidyl ether or the like as the adsorbent for selectively removing ET from a solution in which highly acid substance such as heparin coexists (see Patent literature No. 6, for example). However, the ligand is basically cationic and heparin adsorption is reduced by modification, but cannot be always completely prevented.

Cyclodextrin (hereinafter, also referred to as "CD") is widely known to be a molecule in which glucose is linked in a cyclic manner to include a compound that can be entered into an inside of a cycle. Report has been made on a method for producing CD polymer beads by crosslinking CD with epichlorohydrin (see Patent literature No. 7, Patent literature No. 8 and Patent literature No. 9, for example). Such a CD polymer or a polymer of CD and a polystyrene resin is known to be used as an adsorbent of an environmental hormone such as bisphenol A (see Patent literature No. 10 and Patent literature No. 11, for example). Moreover, such a CD polymer is known to be used for removal of chlorogenic acid from a coffee extract (see Patent literature No. 12, for example). However, no description has been made on use of the CD polymers for removal of ET. Moreover, all of the CD polymers are produced by using epichlorohydrin as a crosslinking agent. In Patent literature No. 8, a di-epoxy compound, diisocyanate, an acrylamide derivative and so forth are exemplified as the crosslinking agent in addition to epichlorohydrin, but no properties of CD polymer produced using a crosslinking agent material other than epichlorohydrin have been disclosed.

Meanwhile, an invention is disclosed in which CD is crosslinked with a diisocyanate compound to prepare a polymer, the polymer is mixed with an aqueous solution of alginic acid, and then the resulting mixture is added dropwise to an aqueous solution of calcium chloride to prepare a spherical CD polymer and a phenolic compound that influences an environment is adsorbed with the spherical polymer (see Patent literature No. 13, for example). However, no arts have been disclosed on adsorption capacity of the phenolic compound with the CD polymer alone before mixing with alginic acid or the like. Moreover, no description has been made on use of the CD polymer produced using the diisocyanate compound as the crosslinking agent for removal of ET.

Moreover, an attempt has been made on adsorption and removal of lipopolysaccharides in blood by us ing a polymer resin obtained by crosslinking CD with a crosslinking agent such as epichlorohydrin (see Patent literature No. 14, for example). However, no description has been made as to whether or not ET can be selectively adsorbed and removed using the CD polymer resin. Moreover, in Patent literature No. 14, isocyanate, polyamine, acrylate and carbonate are exemplified as the crosslinking agent in addition to epichlorohydrin, but no properties of the CD polymer resin produced using a cross linking agent other than epichlorohydrin have been disclosed.

Moreover, an attempt has been made on selectively removing ET from a DNA solution using CD polymer beads obtained by crosslinking CD with epichlorohydrin (see Non-patent literature No. 5, for example). According to the CD polymer beads, adsorption of DNA is hardly caused, and ET can be selectively removed. However, ET that can be adsorbed and removed with the CD polymer beads is about 80% based on the total amount, and about 20 of ET is not removed and remains in the solution. More specifically, the CD polymer beads have had room for improvement in view of ET adsorption capacity.

Moreover, report has been made on a method for producing nucleic acid and/or oligonucleotide containing no or reduced ET for a gene therapy (see Patent literature No. 15). Patent literature No. 15 discloses a method for treating a nucleic acid solution subjected to ET removal treatment beforehand with a surfactant-containing ET removal buffer or with an alkali-containing buffer or SDS-containing buffer, or a nucleic acid solution subjected ET removal treatment by nickel chelate chromatography or chromatography using polymyxin, DNA ETOX or the like by using a support of inorganic chromatography or an ion exchanger for holding DNA with a high salt concentration to purify DNA. However, the method is significantly complicated and requires a large number of solvents and reagents such as salts, and much time.

CITATION LIST

Patent Literature

Patent literature No. 1: JP S59-193135 A.
Patent literature No. 2: JP 3817808 B.
Patent literature No. 3: JP 2000-189792 A.
Patent literature No. 4: JP H4-256438 A.
Patent literature No. 5: JP 2002-263486 A.
Patent literature No. 6: JP 2007-145743 A.
Patent literature No. 7: JP S60-11961 B.
Patent literature No. 8: JP S60-20924 A.
Patent literature No. 9: JP 2006-143953 A.
Patent literature No. 10: JP 2003-226737 A.
Patent literature No. 11: JP 2003-226755 A.
Patent literature No. 12: JP H7-322823 A.
Patent literature No. 13: JP 4683632 B (JP 2006-83379 A).
Patent literature No. 14: JP 2009-502905 A.
Patent literature No. 15: JP H9-508406 A Non-Patent Literature Non-patent literature No. 1: Isserkutz A. C., J. Immunol. Methods 61, 275-281 (1983).
Non-Patent Literature No. 2: Phillip M. Montbriand, et al., Journal of Biotechnology 44 (1996) 43-46.
Non-patent literature No. 3: Chuichi H., et al., Journal of Chromatography B, 781 (2002) 419-432.
Non-Patent Literature No. 4: Dagmar Petsch, et al., Journal of Biotechnology 76 (2000) 97-119.
Non-Patent Literature No. 5: Masayo Skata, et al., ANALYTICAL SCIENCES FEBRUARY (2011) VOL. 27.

SUMMARY OF INVENTION

Technical Problem

As a material for adsorbing and removing endotoxin (ET), an adsorbent using as a ligand a basic antibiotic such as polymyxin, an adsorbent using as a ligand a polycation such as polylysine, poly(ε-lysine), polyethyleneimine and polyallylamine, or an adsorbent prepared by introducing a positive charge such as an amino group into an insoluble carrier has been developed and used so far. However, no ET can be selectively removed under coexistence of nucleic acid such as DNA by using the adsorbents. On the other hand, ET can be selectively removed under coexistence of DNA by using a CD polymer obtained by crosslinking CD with epichlorohydrin, but the polymer has had room for improvement in view of ET adsorption capacity. An object of the invention is to provide a means for selectively removing ET under coexistence of a substance showing a negative charge such as nucleic acid, and an endotoxin adsorbent (ET adsorbent) that can be utilized for the means.

Solution to Problem

The present inventors have diligently continued to conduct study in order to attain the object, and as a result, have found that ET can be selectively removed under coexistence of a negative charge such as nucleic acid by using polymer particles obtained by crosslinking cyclodextrin with an isocyanate-based crosslinking agent, and thus have completed the invention.

More specifically, the invention includes structures described below.

Item 1. Polymer particles of cyclodextrin, having features (1) to (4) described below:
(1) N/C shown according to the following formula is 6 to 15;

$$N/C(\text{mol \%}) = \text{nitrogen content(mol)/carbon content (mol)} \times 100 \quad \text{(formula 1)}$$

(2) part of hydroxy group of cyclodextrin forms a urethane bond;
(3) insoluble in water; and
(4) anion exchange capacity is less than 0.1 meq/g.

Item 2. A method for producing the polymer, comprising allowing a crosslinking agent to react with cyclodextrin, wherein
the crosslinking agent is a compound having one or more isocyanate groups, per molecule, and one or more functional groups that can react with a hydroxy group.

Item 3. The method, wherein the functional group that can react with the hydroxy group is an isocyanate group.

Item 4. An endotoxin adsorbent, containing a base material and the polymer immobilized to the base material.

Item 5. A method for producing the endotoxin adsorbent, comprising immobilizing of the polymer to a base material.

Item 6. A method for producing the endotoxin adsorbent, comprising allowing a crosslinking agent to react with a base material, and cyclodextrin, wherein the crosslinking agent is a compound having one or more isocyanate groups, and one or more functional groups that can react with a hydroxy group.

Item 7. The method, wherein the functional group that can react with the hydroxy group is an isocyanate group.

Item 8. A method for removing endotoxin, comprising bringing a solution containing an objective material showing a negative charge and endotoxin into contact with the polymer or the adsorbent.

Item 9. A method for producing a solution containing an objective material showing a negative charge from which endotoxin is removed, comprising bringing a solution containing an objective material showing a negative charge and endotoxin into contact with the polymer or the adsorbent.

Item 10. The method, wherein the objective material showing the negative charge is nucleic acid.

Item 11. The method, wherein the nucleic acid is DNA.

Item 12. The method, wherein the nucleic acid is RNA.

DESCRIPTION OF EMBODIMENTS

Figure 1:
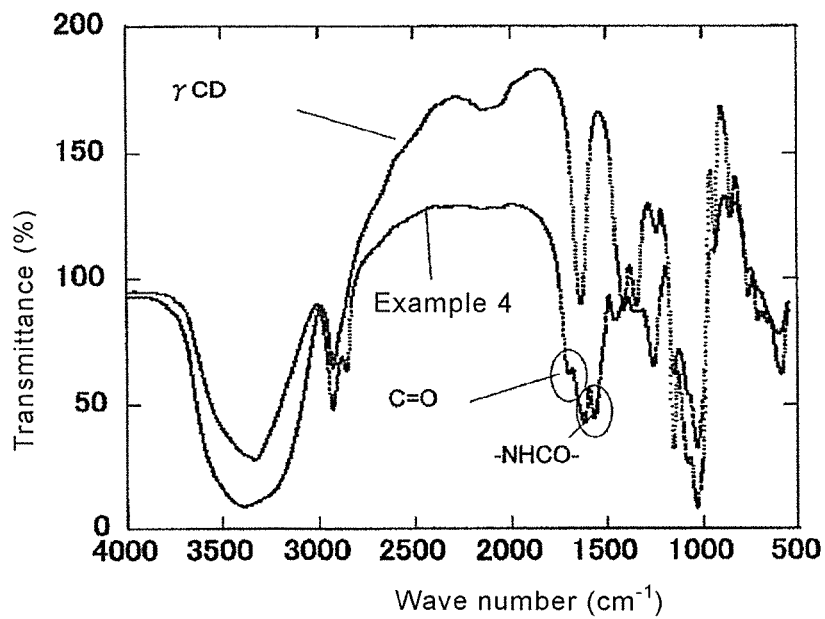
FIG. 1 is drawing showing an IR chart of γCD and a CD polymer in Example 4.

The invention will be described in detail below.

A first item according to the invention concerns a polymer of cyclodextrin (CD) having the following features (1) to (4) (hereinafter, also referred to as "CD polymer according to the invention"):

(1) containing a nitrogen atom of 6 to 15 in a mole ratio based on a carbon atom:

(2) part of hydroxy group of cyclodextrin forms a urethane bond;

(3) insoluble in water; and (4) substantially showing no anion exchange capacity.

CD is a compound having cyclic structure in which a plurality of molecules of D-glucose are bonded by an α-1,4 glycoside bond. CD is known to include various kinds of organic molecules in a cavity thereof. Specific examples of CD include α-cyclodextrin, β-cyclodextrin and γ-cyclodextrin. Each feature is shown in Table 1. In the table, "glucose unit" means the number of glucose molecules that form one molecule of CD, namely, the number of glucose molecules that form the cyclic structure of CD.

TABLE 1

| Name | glucose unit | Molecular weight | Cavity diameter | CAS No. |
|---|---|---|---|---|
| α-cyclodextrin | 6 | 972 | About 0.6 nm | 10016-20-3 |
| β-cyclodextrin | 7 | 1,135 | 0.7 to 0.8 nm | 7585-39-9 |
| γ-cyclodextrin | 8 | 1,297 | 0.9 to 1.0 nm | 17465-86-0 |

The CD polymer has structure in which CD is crosslinked. The CD polymer of the invention is obtained by crosslinking CD with a crosslinking agent as described later, for example. In the CD polymer of the invention, one kind of CD may be crosslinked, or two or more kinds of CD may be crosslinked. When two or more kinds of CD are crosslinked, a ratio of each CD is not particularly restricted, and persons skilled in the art may appropriately select the ratio.

The CD polymer of the invention contains the nitrogen atom of 6% to 15% in the mole ratio based on the carbon atom. More specifically, in the CD polymer of the invention, N/C (mol %) shown in the formula 1 below is 6 to 15. The nitrogen content and the carbon content according to the invention are determined by an elemental analysis. The elemental analysis is conducted according to a combustion method.

$$N/C(\text{mol \%}) = \text{nitrogen content(mol)/carbon content (mol)} \times 100 \quad \text{(formula 1)}$$

The CD polymer of invention is insoluble in water. In the invention, "insoluble in water" means that solubility of the CD polymer of the invention in water is less than 1 mg/L at 25° C., preferably, less than 1 μg/L, and further preferably, 0 μg/L.

The CD polymer of the invention substantially shows no anion exchange capacity. In the invention, "substantially shows no anion exchange capacity" means that anion exchange capacity (AEC) of the CD polymer according to the invention is less than 0.1 meq/g. The CD polymer of the invention may have an anion exchange group or no anion exchange group, as long the anion exchange capacity (AEC) is less than 0.1 meq/g. In the invention, the CD polymer of the invention substantially shows no anion exchange capacity, and thus nonspecific adsorption of an objective material showing a negative charge that coexists with ET can be presumably reduced.

The CD polymer of the invention may have a cation exchange group or no cation exchange group. An amount of the cation exchange group of the CD polymer according to the invention is not particularly restricted, but for example, when a substance having a positive charge exists in an ET solution (a solution containing the objective material showing the negative charge and ET), from a viewpoint of reducing the nonspecific adsorption of the substance having the positive charge, a case where the amount is preferably small is conceivable. For example, the CD polymer of the invention may substantially show no cation exchange capacity. In the invention, "substantially shows no cation exchange capacity" means that the cation exchange capacity (CEC) of the CD polymer according to the invention is less than 0.1 meq/g.

The ion exchange capacity is quantitatively determined according to a pH titration method. Quantitative determination of the ion exchange capacity can be specifically found in the description in Examples.

The ion exchange group may be introduced by a crosslinking reaction or may be introduced separately from the crosslinking reaction, for example. The ion exchange group may be a free ion exchange group or may form a salt.

In the CD polymer of the invention, part of hydroxy group of CD forms the urethane bond. The urethane bond herein refers to structure represented by "(CD)-O—CO—NH—R." In the structure, "(CD)" represents a CD molecule constituting the CD polymer according to the invention, and "R" represents arbitrary structure. In the CD polymer of the invention, all of the CD molecules constituting the CD polymer according to the invention may have the urethane bond, or part of CD molecules may have no urethane bond. The urethane bond can be formed by allowing CD to react with an isocyanate-based crosslinking agent as described later. More specifically, the urethane bond can be formed by bonding of the hydroxy group in the CD molecule with the isocyanate group in the isocyanate-based crosslinking agent as described later. A ratio of the hydroxy group that forms the urethane bond to the total hydroxy groups in the whole CD molecules is appropriately set up depending on various conditions such as a kind of crosslinking agent and N/C (mol %) in the CD polymer according to the invention, for example.

A degree of swelling of the CD polymer according to the invention is not particularly restricted, but may be 2 to 6 or 3 to 5, for example. The degree of swelling means a rate of a volume before drying (measured volume) to dry weight upon drying the CD polymer according to the invention. More specifically, the degree of swelling can be calculated according to formula 3 described below. Measurement of the degree of swelling can be specifically found in the description in Examples.

Degree of swelling(wet-mL/dry-g)=measured volume (mL)/dry weight(g)　　　(formula 3)

A shape of particles of the CD polymer according to the invention is not particularly restricted, but may be granular or spherical, for example. A mean particle diameter of the particles of the CD polymer according to the invention is not particularly restricted, but may be 0.1 micrometer to 500 micrometers, preferably, 10 micrometers to 300 micrometers, and further preferably, 40 micrometers to 150 micrometers, for example. In the invention, "mean particle diameter" means a particle size at 50 of an integrated value in a particle size distribution obtained by laser diffraction and scattering method. The mean particle diameter can be specifically measured using a laser diffraction particle size distribution analyzer, for example.

The CD polymer of the invention can be produced by allowing CD to react with the crosslinking agent, for example. More specifically, the invention provides a method for producing the CD polymer according to the invention, including allowing CD to react with the crosslinking agent. "Crosslinking agent" herein means a compound having one or more isocyanate groups, per molecule, and one or more functional groups that can form a covalent bond with the hydroxy group. In the invention, the crosslinking agent concerned is also referred to as "isocyanate-based crosslinking agent." Specific examples of the functional group that can form the covalent bond with the hydroxy group include a carboxyl group and an isocyanate group. As the functional group that can form the covalent bond with the hydroxy group, an isocyanate group is preferred. More specifically, the crosslinking agent preferably has two or more isocyanate groups per molecule. Specific examples of the compound having two or more isocyanate groups include compounds presented in Table 2 below. The crosslinking agent may also have any other functional group. For example, the crosslinking agent may have an ion exchange group within the range in which advantageous effects of the invention are not adversely affected. As the crosslinking agent, one kind of crosslinking agent may be used or two or more kinds of crosslinking agents may be combined and used.

TABLE 2

| Abbreviation | Compound name | Molecular weight | CAS No. |
| --- | --- | --- | --- |
| HMDI | hexamethylene diisocyanate | 168 | 822-06-0 |
| DIDPM | 4,4'-diphenylmethane diisocyanate | 250 | 101-68-8 |
| IPDI | isophorone diisocyanate | 222 | 4098-71-9 |
| TLDI | tolylene diisocyanate | 174 | 26471-62-5 |
| BIBP | 1,3-bis(2-isocyanato-2-propyl)-benzene | 244 | 2778-42-9 |
| BLMCH | 1,3-bis(isocyanatomethyl)-cyclohexane | 194 | 38661-72-2 |
| DCHMDI | dicyclohexylmethane 4,4'-diisocyanate | 262 | 5124-30-1 |
| TMHMDI | trimethylhexamethylene diisocyanate | 210 | 28679-16-5 |

A reaction (hereinafter, also referred to as "crosslinking reaction") between CD and the isocyanate-based crosslinking agent can be carried out in a suitable solvent. As the solvent, a solvent having no reactivity with the isocyanate group is preferred, for example. Specific examples of the solvent having no reactivity with the isocyanate group include amides such as dimethylacetamide (DMAC) and dimethylformamide (DMF), ethers such as dioxane, diethyl ether and tetrahydrofuran and dimethylsulfoxide. On the other hand, a solvent such as water, alcohol, thiol and amine may be used from a viewpoint of reactivity with the isocyanate group within the range in which the advantageous effects of the invention are not adversely affected, but preferably is not used. As the solvent, one kind of solvent may be used or two or more kinds of solvents may be combined and used.

The crosslinking reaction may be carried out by mixing CD and the crosslinking agent each of which is dissolved in the solvent, by adding the other to the solvent in which one of the CD or the crosslinking agent is dissolved, or by simultaneously dissolving both of CD and the crosslinking agent in the solvent, for example. The crosslinking reaction is preferably carried out by adding the crosslinking agent to the solvent in which CD is dissolved, for example.

Reaction temperature upon carrying out the crosslinking reaction can be appropriately set up depending on various conditions such as a kind of crosslinking agent, a kind of solvent and reaction time. The reaction temperature is not particularly restricted, but may be 10° C. to 100° C., or 50° C. to 90° C., for example.

The reaction time upon carrying out the crosslinking reaction can be appropriately set up depending on various conditions such as a kind of crosslinking agent, a kind of solvent and the reaction temperature. The reaction time is not particularly restricted, but may be 30 minutes to 24 hours, or 1 hour to 10 hours, for example.

A mole ratio (CL/CD) of the crosslinking agent (CL) to CD upon producing the CD polymer of the invention may be 1 to 20, for example. The mole ratio (CL/CD) of the crosslinking agent to CD is preferably 2 to 10 from a viewpoint of strength of the polymer, and further preferably, 3 to 7 from a viewpoint of ET adsorption capacity.

The CD polymer of the invention can be directly utilized as an endotoxin adsorbent (ET adsorbent). More specifically, the invention provides the ET adsorbent formed of the CD polymer of the invention. The CD polymer of the invention may be subjected to processing such as pulverization, and then utilized as the ET adsorbent. When the CD polymer of the invention is produced using only CD and a crosslinking agent having no ion exchange group as raw materials, the CD polymer theoretically has no ion exchange group. Such a CD polymer can be preferably used for adsorption of ET in view of no possibility of the ion exchange group giving an unexpected influence on selective adsorption of ET.

Moreover, the CD polymer of the invention is immobilized to the base material, and can be utilized as the ET adsorbent. More specifically, a second item according to the invention concerns an ET adsorbent containing a base material and a CD polymer immobilized to the base material according to the invention.

In the ET adsorbent in the second item according to the invention, the CD polymer may be immobilized to the base material by the covalent bond or a noncovalent bond. The CD polymer is preferably immobilized to the base material by the covalent bond.

The ET adsorbent in the second item according to the invention can be produced, for example, by immobilizing the CD polymer previously produced according to the invention to the base material. More specifically, the invention provides a method for producing the ET adsorbent, including immobilizing of the CD polymer to the base material according to the present invention. A technique of immobilization can be appropriately selected depending on various conditions such as a kind of functional group of the CD polymer and a kind of functional group of the base material according to the invention.

For example, when the base material having the hydroxy group is used, the CD polymer of the invention can be immobilized to the base material by crosslinking the hydroxy group remaining in the CD polymer of the invention and the hydroxy group in the base material with the isocyanate-based crosslinking agent. More specifically, the immobilization can be performed by allowing the base material and the CD polymer of the invention to react with the isocyanate-based crosslinking agent, for example. The immobilization can be performed in the suitable solvent as described above. Moreover, the description on the reaction temperature and the reaction time of the crosslinking reaction upon producing the CD polymer of the invention may be correspondingly applied to reaction temperature and reaction time for the immobilization.

The immobilization may be performed, for example, by mixing the base material, the CD polymer of the invention, and the cross linking agent that are dissolved or dispersed into solvents, respectively, by dissolving or dispersing the base material, the CD polymer of the invention and the crosslinking agent into the solvent at arbitrary order, or by simultaneously dissolving or dispersing the base material, the CD polymer of the invention and the crosslinking agent into the solvent. The CD polymer of the invention is subjected to processing such as pulverization and then may be the provided for the immobilization.

The ET adsorbent in the second item according to the invention can also be produced by allowing the base material and CD to react with the isocyanate-based crosslinking agent, for example. More specifically, the invention provides a method for producing the ET adsorbent including allowing the base material and CD to react with the isocyanate-based crosslinking agent. The reaction can be carried out in the suitable solvent as described above. Moreover, the description on the reaction temperature and the reaction time of the crosslinking reaction upon producing the CD polymer of the invention as described above may be correspondingly applied to reaction temperature and reaction time for the method.

The reaction may be carried out, for example, by mixing the base material, CD, and the crosslinking agent that are dissolved or dispersed into solvents, respectively, by dissolving or dispersing the base material, CD and the crosslinking agent into the solvent at arbitrary order, or by simultaneously dissolving or dispersing the base material, CD and the crosslinking agent into the solvent. The reaction may be carried out, for example, by adding the crosslinking agent to the solvent in which CD is dissolved to progress the crosslinking reaction, and subsequently adding the base material.

In addition, "allowing the base material and CD to react with the isocyanate-based crosslinking agent" includes, as long as the base material, CD and the isocyanate-based crosslinking agent are used as the raw materials, a case where the base material itself forms the covalent bond with the isocyanate-based crosslinking agent, or CD condensed therewith, and also a case where the base material itself forms no covalent bond with the isocyanate-based crosslinking agent, or CD condensed therewith, but the ET adsorbent to which the CD polymer is immobilized by the noncovalent bond.

The base material is not particularly restricted, if the CD polymer of the invention is immobilized to the base material and can be used as the ET adsorbent. Specific examples of the base materials include an already known adsorbent or a carrier for chromatography, a filter paper, a membrane, a filter, a hollow fiber, a fiber, a polymer that can be processed into a nanofiber and an inorganic material. Specific examples of the base materials include polysaccharideses such as cellulose, agarose, starch, amylose, dextran, pullulan and glucomannan; polyacrylic acid or a derivative thereof, a synthetic polymer such as polyvinyl alcohol, nylon, polysulfone, polyacrylonitrile, polyethylene, polypropylene and polystyrene; and an inorganic material such as glass, porous glass, silica gel and hydroxyapatite. The base material preferably has the functional group for immobilizing the CD polymer of the invention by the covalent bond (hereinafter, also referred to as "functional group for immobilization"). Specific examples of the functional groups for immobilization include a functional group that can form the covalent bond with the hydroxy group in the CD polymer when the CD polymer is directly bonded with the base material. Specific examples of the functional group for immobilization include a functional group that can form the covalent bond with the functional group in the compound when the CD polymer is bonded with the base material through any other compound such as the crosslinking agent. The base material preferably has the hydroxy group, for example, in consideration of capability of immobilizing the CD polymer of the invention to the base material using the isocyanate-based crosslinking agent. Specific examples of the base material having the hydroxy group include polysaccharides. As the polysaccharides, for example, cellulose, agarose or dextran has particularly an operating experience as the carrier for chromatography, and can be particularly preferably used. "Functional group for immobilization" may include a functional group essentially of the base material, or a functional group introduced into the base material. For example, silica gel into which diol is introduced can be used as the base material. Introduction of diol into the silica gel can be performed, for example, by epoxidizing the silica gel, and adding a water molecule thereto to allow ring opening. The description in Examples can be specifically found for introduction of diol to the silica gel. As the base material, one kind of base material may be used or two or more kinds of base materials may be combined and used.

ET can be removed from a solution containing ET by bringing the CD polymer being the first item according to the invention (including the ET adsorbent formed of the identical polymer) or the ET adsorbent being the second item according to the invention into contact with the solution containing ET. In addition, the CD polymer being the first item according to the invention (including the ET adsorbent formed of the identical polymer) and the ET adsorbent being the second item according to the invention are also generically referred to as "ET adsorbent of the invention."

ET is also referred to as lipopolysaccharide, and is a substance in which polysaccharide is bonded with lipid A to which lipid is bonded with phosphorylated saccharide, and a substance showing the negative charge. The ET adsorbent of the invention is useful for selectively removing ET, particularly, when ET and a substance showing the negative charge other than ET coexist. In addition, such a substance showing the negative charge other than ET in the invention is also referred to as "objective material showing the negative charge."

More specifically, a third item according to the invention concerns the method for removing ET (hereinafter, also referred to as "method for removing ET according to the invention") including bringing the ET adsorbent of the invention into contact with a solution containing ET and the objective material showing the negative charge. In the following, the solution containing ET and the objective material showing the negative charge is also referred to as "ET solution." The ET solution may include a solution containing ET and an objective material originally showing the negative charge, or may be a solution prepared by dissolving an objective material contaminated with ET to show the negative charge in the solvent.

Moreover, a solution containing the objective material showing the negative charge from which ET is removed is obtained by the method for removing ET according to the invention. More specifically, one aspect of the method for removing ET according to the invention is a method for producing the solution containing the objective material showing the negative charge from which ET is removed, including bringing the ET adsorbent of the invention into contact with the solution containing ET and the objective material showing the negative charge. The objective material showing the negative charge from which ET is removed is obtained by collecting the objective material showing the negative charge from the solution from which ET is removed obtained by the identical method.

In the invention, "substance showing the negative charge" means a substance having a functional group that tends to become an anion in the molecule. "Functional group that tends to become the anion" means a functional group that can be the anion in an arbitrary solution containing the substance having the functional group. Specifically, the functional group that can be the anion in the ET solution includes "functional group that tends to become the anion," for example. More specifically, "substance showing the negative charge" may show the negative charge in the arbitrary solution containing the substance in the ET solution, for example. Specific examples of "functional group that tends to become the anion" include a carboxyl group, a sulfate group and a phosphate group.

In the invention, "objective material showing the negative charge" is not particularly restricted, if the material is the substance showing the negative charge other than ET. Specific examples of "objective material showing the negative charge" include proteins, peptides, hormones, polysaccharides, nucleic acids, lipids, vitamins and various artificial polymers. Specific examples of protein or peptide showing the negative charge include protein or peptide containing an acidic amino acid residue. Specific examples of the acidic amino acid residue include a glutamic acid residue and an aspartic acid residue. Specific examples of the polysaccharides showing the negative charge include a polyanion derivative of polysaccharides, such as carboxy methyl cellulose and sulfated cellulose, and glucosaminoglycan such as heparin, hyaluronic acid and chondroitin sulfate. Nucleic acid is an acidic substance in which a large amount of phosphate is contained in a molecule, and specific examples of the nucleic acid include DNA and RNA. In the method for removing ET according to the invention, ET can be preferably selectively removed under coexistence of nucleic acid. Specific examples of the artificial polymer showing the negative charge include polyacrylic acid. The "objective materials showing the negative charge" may be a natural product, for example, a substance derived from organism, or an artificially modified or synthesized substance.

In the method for removing ET according to the invention, the ET solution may be appropriately subjected to treatment such pretreatment before contact with the ET adsorbent of the invention. For example, the ET solution may be diluted or concentrated. Moreover, pH of the ET solution may be adjusted and does not need to be adjusted. Although pH is not particularly restricted, pH may be 3 to 10, preferably, 4 to 9, and further preferably, 4 to 6, for example. Then, pH may be adjusted in consideration of stability in each pH of the objective material showing the negative charge in the ET solution, for example. Adjustment of pH can be performed using a buffer, for example. A kind of buffer is not particularly restricted, and can be appropriately selected according to desired pH, for example. Ionic strength of the ET solution is not particularly restricted, and may be adjusted and does not need to be adjusted.

In the method for removing ET according to the invention, the ET adsorbent of the invention may be directly used or may be used after appropriately applying treatment such as processing. For example, when the ET adsorbent of the invention has a shape suitable for the carrier for chromatography, such as a granular form or a membrane form, the ET adsorbent of the invention can be packed into a column, and thus used.

Contact of the ET adsorbent of the invention with the ET solution can be performed by charging the ET adsorbent of the invention into the ET solution, for example. Such a technique is also referred to as a batch process. The solution from which ET is removed is obtained by adsorbing ET onto the charged adsorbent, and then removing the adsorbent from the solution.

For example, when the ET adsorbent of the invention is packed into the column, and thus used, the ET adsorbent of the invention can be brought in contact with the ET solution by feeding the ET solution into the column into which the ET adsorbent of the invention is packed. For example, when the ET adsorbent of the invention is in a filter form, the ET adsorbent of the invention can be brought in contact with the ET solution by feeding the ET solution into a filter-form adsorbent. As such a fluidizing separation method, such a method can be utilized as chromatography including liquid chromatography, membrane chromatography and monolith chromatography; filtration using a hollow fiber, a flat membrane, a membrane filter and a filter paper; solid phase extraction; and an adsorption column for bodily fluid purification.

In the method for removing ET according to the invention, time in contact of the ET adsorbent of the invention with the ET solution in the batch process or a flow rate of the ET solution in the fluidizing separation method is not particularly restricted, but can be appropriately set up depending on various conditions such as a content of ET in the ET solution, and a content or a kind of the objective material showing the negative charge. Moreover, temperature in the method for removing ET according to the invention is not particularly restricted, but can be appropriately set up depending on various conditions such as a kind of the objective material showing the negative charge.

ET in the solution is removed by the method for removing ET according to the invention. "ET is removed" means that the content of ET in the solution is not particularly restricted, if the content is decreased in comparison with the content before treatment (before contact with the ET adsorbent of the invention), but the content of ET in the solution may be decreased to 30% or less, 20% or less, 10% or less, 5% or less or 1% or less in comparison with the content before treatment (before contact with the ET adsorbent of the invention), for example. In the method for removing ET according to the invention, an amount of the objective material showing the negative charge remains is not particularly restricted, if the objective material showing the negative charge remains in an desired amount in the solution after treatment (after contact with the ET adsorbent of the invention), but the objective material showing the negative charge preferably is not substantially removed. "Objective material showing the negative charge is not substantially removed" means that the objective material showing the negative charge in the solution may remain in an amount of 90% or more, 95% or more, 97% or more or 99% or more in comparison with the amount before treatment (before contact with the ET adsorbent of the invention), for example.

EXAMPLES

The invention will be further specifically described by way of Examples and Comparative Examples below, but the invention is not limited to the Examples.

(1) Synthesis of CD Polymer (1-1) Synthesis of CD Polymers in Examples 1 to 18

To 70 mL of N,N-dimethylformamide (DMF) solution, 10 g of cyclodextrin (CD) was gradually added, and dissolved. The resulting CD solution was put in a 500 mL three-necked flask, and stirred at 70° C. for 10 minutes. An isocyanate-based crosslinking agent was added to the flask, and then the resulting mixture was stirred for 4 hours under conditions of 70° C. and 200 rpm. The resulting product was transferred onto a glass filter (G3), and washing and suction filtration were repeated using pure water until a DMF odor was completely lost. Particles having a size diameter of 20 to 105 μm were collected from the resulting product using a sieve to obtain CD polymers in Examples 1 to 18. The CD polymers were stored in 95% methanol.

A kind and an amount of addition of CD used, and a kind and an amount of addition of the crosslinking agent used are shown in Table 3. Abbreviations of the crosslinking agents are as presented in Table 2.

(1-2) Synthesis of CD Polymers in Comparative Examples 1 to 3

CD polymers in Comparative Examples 1 to 3 were synthesized in a manner similar to the synthesis of CD polymers in Examples 1 to 18 except that epichlorohydrin (also referred to as chloromethyl oxirane (CMO)) was used as a crosslinking agent. A kind and an amount of addition of CD used, and a kind and an amount of addition of the crosslinking agent used are shown in Table 3.

TABLE 3

| Sample name | CD Kind | Charge g | Crosslinking agent (CL) Kind | Charge g | CL/CD Mole ratio |
|---|---|---|---|---|---|
| Example 1 | γ | 10 | HMDI | 3.9 | 3 |
| Example 2 | γ | 10 | HMDI | 5.2 | 4 |
| Example 3 | γ | 10 | HMDI | 6.5 | 5 |
| Example 4 | γ | 10 | HMDI | 7.8 | 6 |
| Example 5 | γ | 10 | HMDI | 9.1 | 7 |
| Example 6 | γ | 10 | TMHMDI | 4.9 | 3 |
| Example 7 | γ | 10 | DCHMDI | 6.1 | 3 |
| Example 8 | γ | 10 | BIMCH | 4.5 | 3 |
| Example 9 | γ | 10 | BIPB | 5.6 | 3 |
| Example 10 | γ | 10 | TLDI | 4.0 | 3 |
| Example 11 | γ | 10 | IPDI | 5.1 | 3 |
| Example 12 | γ | 10 | DIDPM | 5.8 | 3 |
| Example 13 | β | 10 | HMDI | 5.9 | 4 |
| Example 14 | β | 10 | TMHMDI | 5.6 | 3 |

TABLE 3-continued

| Sample name | CD Kind | Charge g | Crosslinking agent (CL) Kind | Charge g | CL/CD Mole ratio |
|---|---|---|---|---|---|
| Example 15 | β | 10 | PIPB | 6.4 | 3 |
| Example 16 | α | 10 | HMDI | 6.9 | 4 |
| Example 17 | α | 10 | TLDI | 5.4 | 3 |
| Example 18 | α | 10 | PIPB | 7.5 | 3 |
| Comparative Example 1 | α | 10 | CMO | 14.3 | 15 |
| Comparative Example 2 | β | 10 | CMO | 9.8 | 12 |
| Comparative Example 3 | γ | 10 | CMO | 8.6 | 12 |

(2) Measurement of Amount of Introduction of Isocyanate Group

An amount of introduction of an isocyanate group in the CD polymer obtained as described above was determined by an elemental analysis after drying the CD polymer under reduced pressure. CD has no nitrogen atom, and a measured nitrogen content is derived from the isocyanate group in the crosslinking agent. Results are presented in Table 4.

TABLE 4

Table 4 N/C Ratio (mol %) of CD Polymer

| Sample name | CD Kind | Crosslinking agent (CL) Kind | CL/CD Mole ratio | Elemental analysis N/C (mol %) |
|---|---|---|---|---|
| Example 1 | γ | HMDI | 3 | 8.5 |
| Example 2 | γ | HMDI | 4 | 12.3 |
| Example 3 | γ | HMDI | 5 | 12.4 |
| Example 4 | γ | HMDI | 6 | 13.4 |
| Example 5 | γ | HMDI | 7 | 14.6 |
| Example 6 | γ | TMHMDI | 3 | 8.0 |
| Example 7 | γ | DCHMDI | 3 | 7.2 |
| Example 8 | γ | BIMCH | 3 | 8.6 |
| Example 9 | γ | BIPB | 3 | 6.8 |
| Example 10 | γ | TLDI | 3 | 8.4 |
| Example 11 | γ | IPDI | 3 | 8.1 |
| Example 12 | γ | DIDPM | 3 | 7.0 |
| Example 13 | β | HMDI | 4 | 11.5 |
| Example 14 | β | TMHMDI | 3 | 9.4 |
| Example 15 | β | PIPB | 3 | 7.9 |
| Example 16 | α | HMDI | 4 | 13.2 |
| Example 17 | α | TLDI | 3 | 10.0 |
| Example 18 | α | PIPB | 3 | 8.5 |
| Comparative Example 1 | α | CMO | 15 | 0 |
| Comparative Example 2 | β | CMO | 12 | 0 |
| Comparative Example 3 | γ | CMO | 12 | 0 |

In addition, introduction of the isocyanate group into the CD polymer can also be confirmed by measurement of an infrared absorption spectrum. IR charts of γCD and the CD polymer in Example 4 are shown in FIG. 1. In comparison with γCD before crosslinking, the CD polymer was found to have features of having peaks arising from "C=O" or "—NH—CO—."

(3) Measurement of Anion Exchange Capacity

Anion exchange capacity of the CD polymer obtained as described above was quantitatively determined by a pH titration method. First, 5 mL of CD polymer was transferred onto a glass filter, and sequentially washed with methanol, acetone and ether, and then dried under reduced pressure for 24 hours. Then, 0.5 g of the resulting dry CD polymer was weighed, put in a 100 mL Erlenmeyer flask, and an exact amount of 25 mL of 0.1 N-hydrochloric acid aqueous solutions was added thereto. After stirring was performed for 2 hours, the resulting reaction mixture was taken to a 100 mL measuring flask, and adjusted to a constant volume of 100 mL with distilled water. From the diluted solution, 25 mL was fractionated, and titrated with 0.05 N-sodium hydroxide using phenolphthalein as an indicator. A titration operation was repeated three times, and a mean value was used for calculation of anion exchange capacity. The anion exchange capacity (AEC) was determined according to the following formula 2. The results are presented in Table 5. Anion exchange capacity of Cellfibe ET clean L (made by JNC Corporation) and anion exchange capacity of Detoxi-Gel (made by Thermo Fischer Scientific K.K./Pierce Chemical Co.), each being a commercially available ET adsorbent, are also presented therein.

$$AEC(meq/g)=(0.1 \times fHCl \times VHCl - 0.05 \times fNaOH \times VNaOH \times 100/25)/W \quad \text{(formula 2)}$$

fHCl: factor of 0.1 N-hydrochloric acid aqueous solution
fNaOH: factor of 0.05 N-sodium hydroxide aqueous solution
VHCl: amount (mL) of addition of 0.1 N-hydrochloric acid
VNaOH: amount (mL) of titration of 0.05 N-sodium hydroxide aqueous solution
W: weight (g) of dry CD polymer (4) Measurement of Degree of Swelling A CD polymer in an amount of about 3 mL to about 6 mL as a volume was put in a 10 mL measuring flask. Still standing and tapping were repeated until a volume value was stabilized, and then a volume thereof was measured. Next, all of the CD polymers in the measuring flask the volumes of which were measured were collected into a 20 mL beaker, and allowed to stand at 80° C. for 16 hours or more to evaporate moisture and dry the CD polymers, and then dry weight of the CD polymer was measured. A degree of swelling was determined according to the following formula 3. The results are presented in Table 5.

$$\text{Degree of swelling(wet-mL/dry-g)} = \text{measured volume (mL)/dry weight(g)} \quad \text{(formula 3)}$$

TABLE 5

Table 5 Ion Exchange Capacity of CD Polymer

| Sample name | CD Kind | Crosslinking agent (CL) Kind | CL/CD Mole ratio | Anion exchange capacity meq/g | Degree of swelling Wet-mL/dry-g |
|---|---|---|---|---|---|
| Example 1 | γ | HMDI | 3 | <0.1 | 4.2 |
| Example 2 | γ | HMDI | 4 | <0.1 | 4.1 |
| Example 3 | γ | HMDI | 5 | <0.1 | 3.9 |
| Example 4 | γ | HMDI | 6 | <0.1 | 3.5 |
| Example 5 | γ | HMDI | 7 | <0.1 | 3.4 |
| Example 6 | γ | TMHMDI | 3 | <0.1 | 4.1 |
| Example 7 | γ | DCHMDI | 3 | <0.1 | 4.0 |
| Example 8 | γ | BIMCH | 3 | <0.1 | 4.1 |
| Example 9 | γ | BIPB | 3 | <0.1 | 3.9 |
| Example 10 | γ | TLDI | 3 | <0.1 | 4.0 |
| Example 11 | γ | IPDI | 3 | <0.1 | 4.1 |
| Example 12 | γ | DIDPM | 3 | <0.1 | 3.8 |
| Example 13 | β | HMDI | 4 | <0.1 | 4.0 |
| Example 14 | β | TMHMDI | 3 | <0.1 | 4.1 |
| Example 15 | β | PIPB | 3 | <0.1 | 4.1 |
| Example 16 | α | HMDI | 4 | <0.1 | 3.9 |
| Example 17 | α | TLDI | 3 | <0.1 | 3.9 |
| Example 18 | α | PIPB | 3 | <0.1 | 3.8 |
| Comparative Example 1 | α | CMO | 15 | <0.1 | 5.0 |
| Comparative Example 2 | β | CMO | 12 | <0.1 | 5.5 |
| Comparative Example 3 | γ | CMO | 12 | <0.1 | 5.2 |
| Cellfibe ET clean L | | | | 0.6 | 15 |
| Detoxi-Gel | | | | 0.2 | 21 |

(5) Measurement of ET Adsorption Amount of CD Polymer (5-1) Freeing of ET

Freeing of ET in a CD polymer and a commercially available ET adsorbent to be provided for measurement of ET adsorption amount was performed according to the following procedures. Each of CD polymers obtained as described above, and Detoxi-Gel (made by Thermo Fischer Scientific K.K./Pierce Chemical Co.) and Cellfibe ET clean L (made by JNC Corporation), each being the commercially available ET adsorbent, were weighed in an amount of 5 to 10 g, and washing was repeated five times on a sterilized glass filter using 50 mL of a washing solution (95% ethanol solution containing 0.2 M NaOH). Next, a sample after washing was put in a flask for 100 mL, 50 mL of washing solution was added thereto, and the resulting mixture was stirred at 25° C. for 1 hour at 200 rpm. Next, a sample after stirring was washed again on a glass filter five times using 25 mL of washing solution. Further, washing was repeated using distilled water for injection until a filtrate became neutral, and then equilibration was carried out using a phosphate buffer (pH: 6) having an ionic strength of 0.05, and the resulting material was used as an ET-freed adsorbent for subsequent experiments.

(5-2) ET Adsorption Removal According to a Batch Process

An ET adsorption and removal test was conducted, using a phosphate buffer (pH: 6) having an ionic strength of 0.05 and including a predetermined amount of LPS derived from *E. coli* O55-B5 strains as a sample solution, according to the following procedures. Then, 0.1 g of the ET-freed adsorbent obtained as described above was put in a 20 mL Erlenmeyer flask, 2 mL of sample solution was added thereto, and the resulting mixture was stirred at 4° C. for 1 hour at 200 rpm. The resulting suspended solution was sucked up using a syringe, and filtered using a 0.8 μm membrane filter. A residual endotoxin concentration in the resulting filtrate was quantitatively determined. Measurement of the ET concentration was carried out using a commercially available kit (Limulus ES-II test Wako, made by Wako Pure Chemical Industries, Ltd.).

Figure 2:
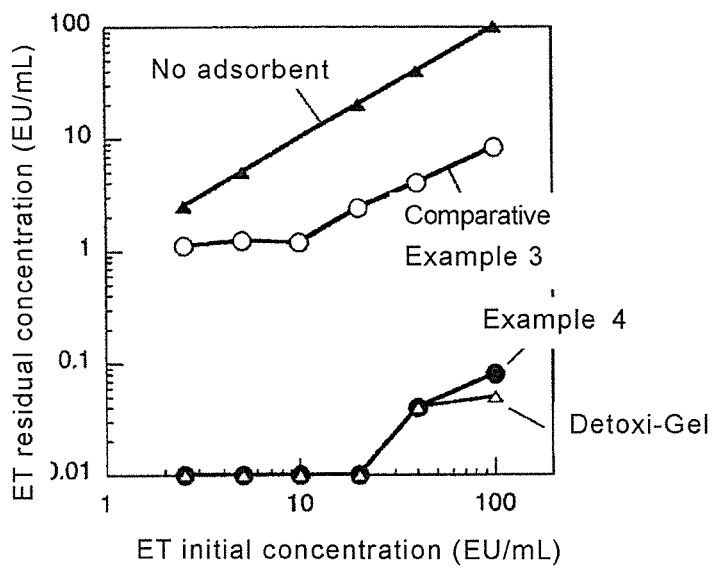
FIG. 2 is a drawing showing ET adsorption capacity of each CD polymer.

The results are presented in Table 6 and FIG. 2. In addition, data in Table 6 and FIG. 2 were obtained in separate batches, respectively. The CD polymer crosslinked with the isocyanate-based crosslinking agent was shown to have a lower residual ET concentration and higher ET removal capacity in comparison with the CD polymer crosslinked with epichlorohydrin (Table 6). Moreover, the CD polymer in Example 4 was found to have ET adsorption capacity equivalent to the capacity of Detoxi-Gel being the ET adsorbent of a commercial item (FIG. 2).

TABLE 6

Table 6 ET Adsorption Amount of CD Polymer

| Sample name | Concentration of endotoxin (EU/mL) | |
|---|---|---|
| | Before treatment | After treatment |
| Example 1 | 1 | <0.01 |
| | 10 | <0.01 |
| | 100 | <0.01 |
| | 1,000 | <0.01 |
| Example 2 | 1 | <0.01 |
| | 10 | <0.01 |
| | 100 | <0.01 |
| | 1,000 | <0.01 |
| Example 3 | 1 | <0.01 |
| | 10 | <0.01 |
| | 100 | 0.05 |
| | 1,000 | 22 |
| Example 4 | 1 | <0.01 |
| | 10 | <0.01 |
| | 100 | 2 |
| | 1,000 | 45 |
| Example 8 | 1 | <0.01 |
| | 10 | <0.01 |
| | 100 | <0.01 |
| | 1,000 | <0.01 |
| Example 10 | 1 | <0.01 |
| | 10 | <0.01 |
| | 100 | <0.01 |
| | 1,000 | 0.05 |
| Example 13 | 1 | <0.01 |
| | 10 | <0.01 |
| | 100 | 0.1 |
| | 1,000 | 10 |
| Example 16 | 1 | <0.01 |
| | 10 | 0.1 |
| | 100 | 5 |
| | 1,000 | 19 |
| Comparative Example 2 | 1 | 0.9 |
| | 10 | 8.8 |
| | 100 | 45 |
| | 1,000 | Unmeasured |
| Comparative Example 3 | 1 | 0.6 |
| | 10 | 2.2 |
| | 100 | 8.0 |
| | 1,000 | Unmeasured |
| Detoxi-Gel | 1 | <0.01 |
| | 10 | <0.01 |
| | 100 | <0.01 |
| | 1,000 | <0.01 |
| ET clean L | 1 | <0.01 |
| | 10 | <0.01 |
| | 100 | <0.01 |
| | 1,000 | <0.01 |

(5-3) ET Adsorption Removal in DNA Solution in Various Levels of Ionic Strength

As a sample solution, a phosphate buffer (pH: 6) having an ionic strength of 0.05 to 0.8 and containing 15 EU/mL of LPS derived from *E. coli* O55-B5 strains and 50 mg of DNA derived from salmon milt was used, and an ET adsorption and removal test was conducted in a manner similar to the procedures in (5-2) A residual endotoxin concentration and a residual DNA concentration in the resulting treated liquid (filtrate) were quantitatively determined, and a relationship between ionic strength and an amount of selective adsorption of ET was investigated. Measurement of an ET concentration was carried out in a manner similar to the procedures (5-2). A DNA concentration was measured based on absorbance at 260 nm.

Figure 3:
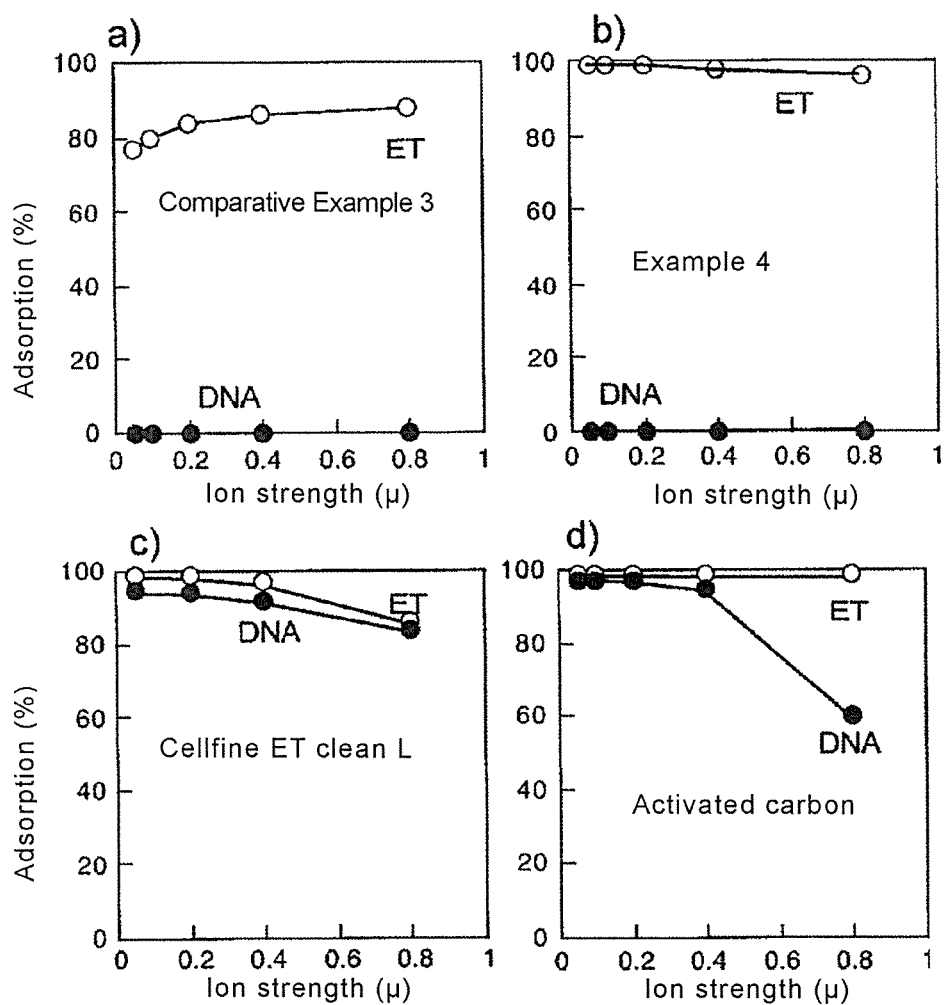
FIG. 3 is a drawing showing a relationship between ionic strength and adsorption capacity for ET and DNA.

The results are shown in FIG. 3. The CD polymer in Example 4 was found to adsorb nearly 100% of ET, and adsorb no DNA at any level of ionic strength. On the other hand, the CD polymer in Comparative Example 3 was found to adsorb no DNA at any level of ionic strength, but have adsorption of ET as lower as about 80% in comparison with Example 4. More specifically, all of the CD polymer in Example 4 and the CD polymer in Comparative Example 3 can selectively adsorb ET under coexistence of DNA, but the CD polymer in Example 4 is further excellent in comparison with the CD polymer in Comparative Example 3 in view of the ET adsorption capacity. Moreover, Cellfine ET clean L and activated carbon, each being a commercially available ET adsorbent, adsorbed both DNA and ET at any level of ionic strength to allow no selective adsorption of ET under coexistence of DNA.

(5-4) ET Adsorption and Removal in DNA Solution in Various Levels of pH

As a sample solution, a buffer (described below) having an ionic strength of 0.05 and pH of 4 to 9 and containing 15 EU/mL of LPS derived from *E. coli* O55-B5 strains and 50 mg of DNA derived from salmon milt was used, and an ET adsorption and removal test was conducted in a manner similar to the procedures in (5-2). A residual endotoxin concentration and a residual DNA concentration in the resulting treated liquid (filtrate) were quantitatively determined, and a relationship between pH and an amount of selective adsorption of ET was investigated. Measurement of an ET concentration was carried out in a similar manner to the procedures (5-2). A DNA concentration was measured based on absorbance at 260 nm.
(Buffer Used)
pH: 4 and 5, acetate buffer ($CH_3COOH$—$CH_3COONa$)
pH: 6 and 7, phosphate buffer ($Na_2HPO_4$—$NaH_2PO_4$)
pH: 8 and 9, Tris buffer (Tris-HCl)

Figure 4:
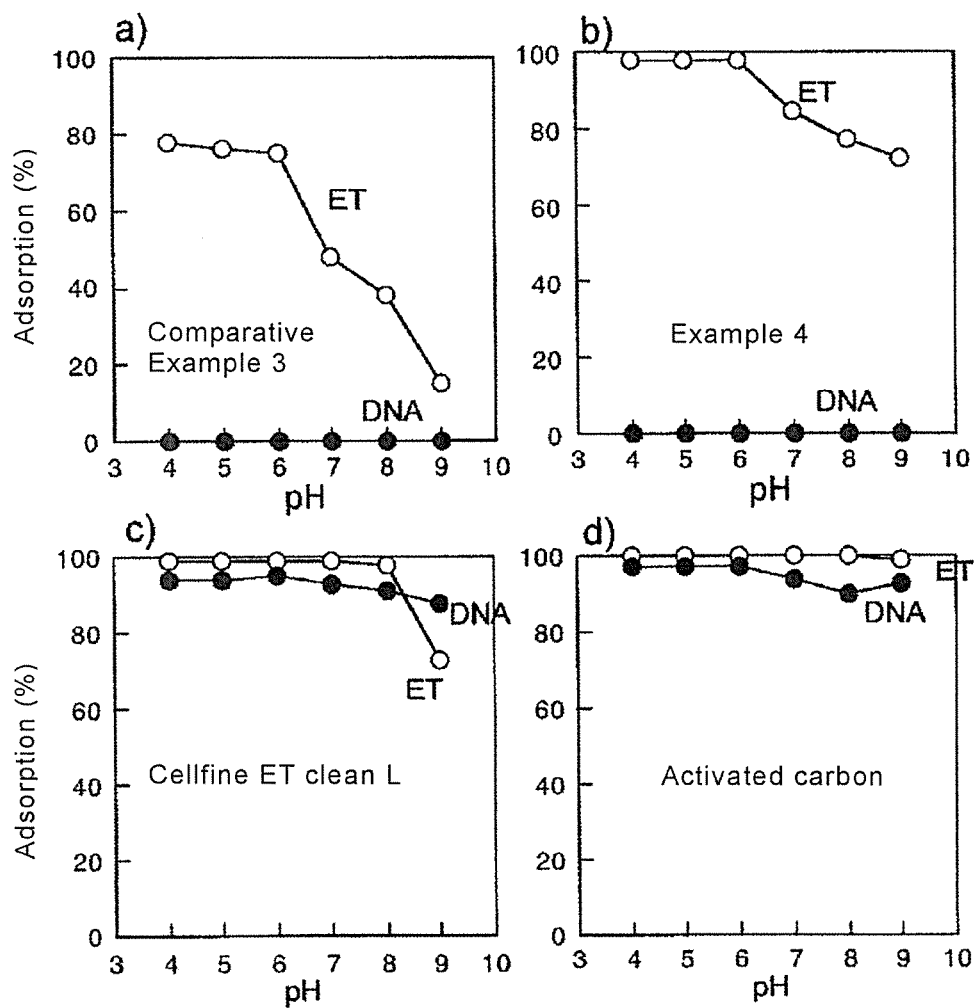
FIG. 4 is a drawing showing a relationship between pH and adsorption capacity for ET and DNA.

The results are shown in FIG. 4. The CD polymer in Example 4 was found to adsorb 70% or more of ET and no DNA at any level of pH. The CD polymer in Example 4 was found to allow adsorption of substantially 100% of ET particularly at pH 4 to pH 6. More specifically, the CD polymer in Example 4 can selectively remove ET from the DNA solution in a wide pH range. On the other hand, the CD polymer in Comparative Example 3 was found to adsorb no DNA at any level of pH to allow absorption of 70% or more of ET at pH 4 to pH 6. More specifically, the CD polymer in Comparative Example 3 can selectively remove ET from the DNA solution particularly at pH4 to pH 6, but the performance is less than the performance in Example 4 in view of the ET adsorption capacity. Moreover, Cell fine ET clean L and activated carbon, each being a commercially available ET adsorbent, adsorbed both DNA and ET at any level of pH to allow no selective adsorption of ET under coexistence of DNA.

(6) Preparation of CD Polymer Immobilized to Silica Base Material (Adsorbent in Example 19)

Then, 20 g of porous silica gel (particle size: 30 μm, mean pore diameter: 1,300 Å) was suspended into 20 g of 3-glycidoxypropyltriethoxysilane and 5 mL of triethylamine, and the resulting mixture was refluxed for 8 hours. After cooling, the silica gel was washed with 400 mL of toluene, 400 mL of methanol, 1 L of pure water, 400 mL of acetone and 400 mL of methanol in the above order, and dried in vacuum at 80° to obtain 26 g of epoxy-introduced silica gel. Then, 20 g of epoxy-introduced silica gel was suspended into 900 mL of 0.7% hydrogen peroxide water and 100 mL of acetonitrile, and the resulting mixture was refluxed for 6 hours. After cooling, the silica gel was washed with 400 mL of toluene, 400 mL of methanol, 1 L of pure water, 400 mL of acetone and 400 mL of methanol in the above order, and dried in vacuum at 80° C. to obtain diol-containing silica gel. To 70 mL of DMF solution, 5 g of γCD was gradually added, and dissolved into the solution. The resulting CD solution was put in a 500 mL three-necked flask, and the resulting mixture was stirred at 70° C. for 10 minutes. To the flask, 2.5 g of HMDI being a crosslinking agent was added, and then the resulting mixture was stirred at 70° C. for 30 minutes at 200 rpm. Then, 10 g of diol-containing silica was added thereto, and the resulting mixture was stirred at 70° C. for 4 hours at 200 rpm. The resulting product was transferred onto a glass filter (G3), and washing and suction filtration were repeated using pure water until DMF odor was completely lost to obtain an adsorbent in Example 19. The adsorbent was stored in 95% methanol.

(7) Preparation of CD Polymer Immobilized to Cellulose Base Material (Adsorbent in Example 20)

Then, 20 g (wet weight) (about 10 g in dry weight) of cellulose particles (mean particle diameter: about 100 μm, exclusion limit molecular weight: 2,500 to 3,500) produced by the method described in JP S53-86749 A was dried at 80° C. to obtain dry cellulose particles. To 70 mL of DMF solution, 5 g of γCD was gradually added, and dissolved into the solution. The resulting CD solution was put in a 500 mL three-necked flask, and the resulting mixture was stirred at 70° C. for 10 minutes. To the flask, 4 g of HMDI being a crosslinking agent was added, and then the resulting mixture was stirred at 70° C. for 30 minutes at 200 rpm. Then, 10 g of dry cellulose particles was added thereto, and the resulting mixture was stirred at 70° C. for 4 hours at 200 rpm. The resulting product was transferred onto a glass filter (G3), and washing and suction filtration were repeated using pure water until DMF odor was completely lost to obtain an adsorbent in Example 20. The adsorbent was stored in 95% methanol.

(8) Preparation of CD Polymer Immobilized to Dextran Base Material (Adsorbent in Example 21)

To 70 mL of DMF solution, 5 g of γCD was gradually added, and dissolved into the solution. The resulting CD solution was put in a 500 mL three-necked flask, and the resulting mixture was stirred at 70° C. for 10 minutes. To the flask, 4 g of HMDI being a crosslinking agent was added, and then the resulting mixture was stirred at 70° C. for 30 minutes at 200 rpm. Then, 10 g (dry weight) of Sephadex G-25 (particle diameter: about 85 to 260 μm, exclusion limit molecular weights: 5,000 or more, GE Healthcare Bioscience Corporation) was added thereto, and the resulting mixture was stirred at 70° C. for 4 hours at 200 rpm. The resulting product was transferred onto a glass filter (G3), and washing and suction filtration were repeated using pure water until DMF odor was completely lost to obtain an adsorbent in Example 21. The adsorbent was stored in 95% methanol.

(9) Preparation of CD Polymer Immobilized to Cellulose Base Material (Adsorbent in Example 22)

To 100 g (wet weight) (about 10 g in dry weight) of cellulose particles (mean particle diameter: about 100 μm, exclusion limit molecular weight: 2,000,000 or more) produced by the method described in JP S55-44312 A, 100 mL of pure water into which 10 g of γCD was dissolved was added, and well mixed. The resulting suspension was dried in vacuum and solidified using an evaporator to obtain a dried product. To 19 g of the dried product, 200 mL of dioxane was added, and the resulting mixture was stirred at 30° C. for 1 hour at 200 rpm. Then, temperature was increased to 80° C., 9 g of HMDI as a crosslinking agent was added thereto, and the resulting mixture was further stirred for 4 hours. The resulting product was transferred onto a glass filter (G3), and washing and suction filtration were repeated using pure water until DMF odor was completely lost to obtain an adsorbent in Example 22. The adsorbent was stored in 95% methanol.

(10) Preparation of CD Polymer Immobilized to Filter Paper (Adsorbent in Example 23)

Then, 0.1 g of the CD polymer in Example 2 was pulverized using a mortar to prepare CD polymer particles having a particle diameter of about 0.1 to 1 μm, and the particles were suspended into 50 mL of DMF. The resulting suspension was circulated into a filter holder (made by Teflon (registered trade name)) in which No. 5C filter paper (6 cmφ) was set to hold the CD polymer particles onto the filter paper. The CD polymer particles almost disappeared in a circulation liquid, and then temperature was raised to 80° C., 1 g of HMDI as a crosslinking agent was added thereto, and the resulting mixture was continuously circulated for 4 hours. The circulation of liquid was suspended, and the resulting product was washed by sequentially flowing 100 mL of methanol and 100 mL of pure water to obtain an adsorbent in Example 23. The adsorbent was stored in 95% methanol.

(11) Adsorption and Removal of ET in DNA Solution Using Adsorbents in Examples 19 to 23

(11-1) ET Removal by Column Chromatography

Into a column having a capacity of 10 mL, 1 mL of each of the adsorbents in Examples 19 to 22 was packed to allow 10 mL of washing liquid (95% ethanol aqueous solution containing 0.2 M NaOH) to pass through the column, and then the adsorbent was immersed into the washing liquid for 3 hours. Then, 10 mL of washing liquid was further passed through the column, and then 50 mL of distilled water for injection was passed therethrough. Subsequently, 5 mL of ET-free 0.2 M phosphate buffer (pH: 7) was passed through the column to equilibrate the column.

Then, 20 mL of phosphate buffer (pH: 7) containing a predetermined amount of LPS derived from *E. coli* O55-B5 strains and DNA derived from salmon milt was passed through the column to collect a column effluent. A residual endotoxin concentration and a residual DNA concentration in the resultant column effluent were quantitatively determined. Measurement of an ET concentration was carried out using a commercially available kit (Limulus ES-II test Wako, made by Wako Pure Chemical Industries, Ltd.). A DNA concentration was measured based on absorbance at 260 nm.

(11-2) ET Removal Using Filter Paper

Through a filter holder in which the adsorbent in Example (filter paper to which the CD polymer was immobilized) was set, 10 mL of washing liquid (95% ethanol aqueous solution containing 0.2 M NaOH) was passed, and then the filter holder was immersed into the washing liquid for 3 hours. Then, 10 mL of washing liquid was further passed through the column, and then 50 mL of distilled water for injection was passed therethrough. Subsequently, 5 mL of ET-free 0.2M phosphate buffer (pH: 7) was passed through the column to equilibrate the column.

Then, 20 mL of phosphate buffer (pH: 7) containing a predetermined amount of LPS derived from *E. coli* O55-B5 strains and DNA derived from salmon milt was passed through the column to collect a column effluent. A residual endotoxin concentration and a residual DNA concentration in the resultant column effluent were quantitatively determined. Measurement of an ET concentration was carried out using a commercially available kit (Limulus ES-II test Wako, made by Wako Pure Chemical Industries, Ltd.). A DNA concentration was measured based on absorbance at 260 nm.

The results are presented in Table 7. All of the adsorbents in Examples 19 to 23 allowed selective adsorption of endotoxin under coexistence of DNA.

TABLE 7

Table 7 Adsorption and Removal of ET in DNA Solution using Adsorbents in Examples 19 to 23

| | Before treatment (initial concentration) | | After treatment (residual concentration) | |
|---|---|---|---|---|
| | DNA µg/mL | ET EU/mL | DNA µg/mL | ET EU/mL |
| Example 19 | 100 | 100 | 96.5 | 0.20 |
| Example 20 | 100 | 100 | 99.0 | 0.08 |
| Example 21 | 100 | 100 | 98.5 | 0.10 |
| Example 22 | 100 | 100 | 99.0 | 0.05 |
| Example 23 | 100 | 100 | 99.5 | 0.30 |

INDUSTRIAL APPLICABILITY

According to an ET adsorbent of the invention, ET can be selectively removed under coexistence of a substance showing a negative charge, such as nucleic acid.

What is claimed is:

1. A method for removing endotoxin, comprising bringing a solution containing an objective material showing a negative charge and endotoxin into contact with a polymer of cyclodextrin or an adsorbent containing a base material and the polymer as immobilized to the base material,
   wherein the polymer has features (1) to (4) described below:
   (1) N/C shown according the following formula is 6 to 15;

$$\text{N/C(mol \%)} = \text{nitrogen content(mol)/carbon content (mol)} \times 100 \quad \text{(formula 1)}$$

(2) part of hydroxy group of cyclodextrin forms a urethane bond;
   (3) insoluble in water; and
   (4) anion exchange capacity is less than 0.1 meq/g.

2. A method for producing a solution containing an objective material showing a negative charge from which endotoxin is removed, comprising bringing a solution containing an objective material showing a negative charge and endotoxin into contact with a polymer of cyclodextrin or an adsorbent containing a base material and the polymer as immobilized to the base material,
   wherein the polymer has features (1) to (4) described below:
   (1) N/C shown according the following formula is 6 to 15;

$$\text{N/C(mol \%)} = \text{nitrogen content(mol)/carbon content (mol)} \times 100 \quad \text{(formula 1)}$$

(2) part of hydroxy group of cyclodextrin forms a urethane bond;
   (3) insoluble in water; and
   (4) anion exchange capacity is less than 0.1 meq/g.

3. The method according to claim 1, wherein the objective material showing the negative charge is nucleic acid.

4. The method according to claim 3, wherein the nucleic acid is DNA.

5. The method according to claim 3, wherein the nucleic acid is RNA.

6. The method according to claim 2, wherein the objective material showing the negative charge is nucleic acid.

7. The method according to claim 6, wherein the nucleic acid is DNA.

8. The method according to claim 6, wherein the nucleic acid is RNA.

9. The method according to claim 1, wherein the solution is brought into contact with the polymer or the adsorbent at pH 4 to 6.

10. The method according to claim 2, wherein the solution is brought into contact with the polymer or the adsorbent at pH 4 to 6.

* * * * *